United States Patent
Modi et al.

(10) Patent No.: US 8,293,918 B2
(45) Date of Patent: Oct. 23, 2012

(54) PROCESS FOR PRODUCING DIHALOPYRIDINES

(75) Inventors: Gelebith H. Modi, Noida (IN); Anil Kumar Tyagi, Noida (IN); Ashutosh Agarwal, Noida (IN); Hem Chandra, Gajraula (IN); Nikhilesh Chandra Bhardwaj, Gajraula (IN); Pradeep Kumar Verma, Gajraula (IN)

(73) Assignee: Jubilant Organosys Limited, Noida (IN)

( * ) Notice: Subject to any disclaimer, the term of this patent is extended or adjusted under 35 U.S.C. 154(b) by 315 days.

(21) Appl. No.: 12/641,926

(22) Filed: Dec. 18, 2009

(65) Prior Publication Data
US 2010/0160641 A1 Jun. 24, 2010

(30) Foreign Application Priority Data
Dec. 19, 2008 (IN) .......................... 2891/DEL/2008

(51) Int. Cl.
*C07D 211/72* (2006.01)

(52) U.S. Cl. .................................................. 546/345
(58) Field of Classification Search .................. None
See application file for complete search history.

(56) References Cited

FOREIGN PATENT DOCUMENTS
WO   WO 2005070888 A2 *   8/2005

OTHER PUBLICATIONS

Kovacic J Amer Chem Soc 1954 vol. 76 pp. 5491-5494.*
Streitwieser, A. et al., Introduction to Organic Chemistry, 4th ed., 1992, p. 793.*
Sigma-Aldrich Catalogue, 2009-2010, p. 2717.*

* cited by examiner

*Primary Examiner* — Janet Andres
*Assistant Examiner* — Heidi Reese
(74) *Attorney, Agent, or Firm* — Oblon, Spivak, McClelland, Maier & Neustadt, L.L.P.

(57) ABSTRACT

Disclosed herein an improved process for producing 2,3-dihalopyridine with high purity at industrial scale with minimum effluent.

23 Claims, No Drawings

US 8,293,918 B2

PROCESS FOR PRODUCING DIHALOPYRIDINES

FIELD OF THE INVENTION

This invention, in general, relates to an improved process for producing dihalopyridines. More particularly, the present invention provides an improved and cost effective process for large-scale industrial production of 2,3-dihalopyridine with high purity.

BACKGROUND OF THE INVENTION 2,3-Dihalopyridine compounds especially 2,3-dichloropyridine are important intermediates for fine chemical industry. The 2,3-dichloropyridine is an important raw material for the preparation of agrochemicals, pharmaceutical and other fine chemicals.

Several processes are reported in the prior art for the preparation of 2,3-dihalopyridine. The known processes differ from each other in respect of different process chemistry followed.

U.S. Pat. No. 4,515,953 and SU652177 disclose the liquid phase chlorination of pyridine or pyridine hydrochloride. The products obtained by this process include 2,3-dichloropyridine along with other polychlorinated pyridine mixture. A number of purification steps are required to extract 2,3-dichloropyridine.

U.S. Pat. No. 6,224,2631 and research article by Bay et al in J. Org. Chem. 1988, 53, 12, 2858-9 disclose a process for the preparation of 2,3-dichloropyridine by halogenetion of 2-chloro-3-nitropyridine with phenylphosphorous tetrachloride (PPTC) and benzenephosphorous dichloride (BPOD).

Shiao et al in Synthetic Communications, 1990, 20, 19, 2971-7 reported synthesis of halogenated 2-chloropyridines by transformation of halogenated 2-methoxypyridines under Vilsmeier-Haack conditions.

JP 01193246 discloses a process for the preparation of 2,3-dichloropyridine where 2,3,6-trichloropyridine formed during the process is reduced with hydrogen in the presence of Pd/C as catalyst.

Den Hertog et al in Rec. Des Tray. Chimi. Des Pays-Bas et de la Belgique, 1950, 69, 673-99; disclosed the preparation of several derivatives of chloropyridines. The research paper discloses a process for the preparation of 2,3-dichloropyridine by treating 2-chloro-3-aminopyridine with sodium nitrite, copper powder and hydrochloric acid. However, the article does not disclose clear process for extraction and purification of 2,3-dichloropyridine.

PCT application WO 2005070888 discloses a four-step process for preparing 2,3-dichloropyridine in which 3-amino-2-chloropyridine is contacted with an alkali metal nitrite in the presence of aqueous hydrochloric acid to form a diazonium salt; subsequently the diazonium salt is decomposed in the presence of copper catalyst wherein at least about 50% of the copper is in the copper (II) oxidation state, optionally in the presence of an organic solvent, to form 2,3-dichloropyridine. 3-amino-2-chloropyridine used in the process is prepared in three steps involving Hofmann rearrangement of nicotinamide to form 3-aminopyridine, contacting 3-aminopyridine with hydrochloric acid to form a 3-aminopyridine hydrochloric acid salt; chlorination of 3-aminopyridine hydrochloric acid salt with a chlorinating agent viz., chlorine or a mixture of hydrochloric acid and hydrogen peroxide to form 3-amino-2-chloropyridine.

CN 1807414 discloses a process for the preparation of 2,3-dichloropyridine. The process comprises of chlorinating 3-aminopyridine with oxydol at a molar ratio of 1:1 in concentrated hydrochloric acid at 6-8° C. for 1-2 h; diazotization of 2-chloro-3-aminopyridine by reacting with 30% sodium nitrite solution at <0° C. for 0.5-1 h; followed by chlorination with a mixture of cuprous chloride and concentrated hydrochloric acid at <0° C. for >30 min; heating reaction liquid to room temperature and extraction with 5-7 times (mass) of dichloromethane (twice) at room temperature; and decompressing and vaporizing the extract to remove the solvent to obtain 2,3-dichloropyridine.

JP 09227522 discloses a process for the separation of 2-chloro-3-aminopyridine from acidic aqueous solution containing 2-chloro-3-aminopyridine and 2,6-dichloro-3-aminopyridine, obtained by chlorination of 3-aminopyridine with chlorine in the presence of hydrochloric acid and $FeCl_3$ at 40° C. for 1 h. The reaction mixture so obtained is mixed with toluene; adjusted to pH 0.5 with aqueous $NH_3$, further adjusting the aqueous layer to pH 7 with aqueous $NH_3$ and extraction with organic solvents to obtain pure 2-chloro-3-aminopyridine.

Krapcho and Haydar in Heterocyclic Communications, 1998, 4, 291-292 reported a process for the preparation of 2,3-dibromopyridine. The process involves temperature dependent displacements of chloride by bromide during the diazotization of 3-amino-2-chloropyridine, followed by addition of CuBr in 48% HBr, which results in high yield of 2,3-dibromopyridine. Additionally, the paper reported the preparation of 2,3-dibromopyridine via the hydrogenation reaction of 2,3,6-tribromopyridine and 1-methyl-4-nitrosobenzene on Pd/C.

Bouillon et al in Tetrahedron, 2002, 58, 17, 3323-3328 reported a three-step process for the preparation of 2,3-dibromopyridine from 2-amino-3-nitropyridine. The process involves diazotization of 2-amino-3-nitropyridine followed by addition of CuBr in 47% HBr to obtain 2-bromo-3-nitropyridine. The 2-bromo-3-nitropyridine so obtained is reduced with Fe and acetic acid to 3-amino-2-bromopyridine and subsequent diazotization to give 2,3-dibromopyridine.

Menzel et al in J. Org. Chem., 2006, 71, 5, 2188-2191 reported an improved method for the bromination of metalated haloarenes employing lithium, zinc transmetalation. In the prior processes the bromination of 2-bromo-3-lithium pyridine resulted in formation of 2,3-dibromopyridine in only 13% yield, whereas in the disclosed process after transmetalation to zinc, 2,3-dibromopyridine was formed in 90% yield.

Very few methods have been reported in the prior art for the preparation of 2,3-difluoropyridine. U.S. Pat. No. 5,498,807 and EP 667328 disclose process for the preparation of 2,3-difluoropyridine by reductive dechlorination of 2,3-difluoro-5-chloropyridine.

Finger et al in J. Org. Chem., 1962, 27, 3965-8 reported a process for the preparation of 2,3-difluoropyridine from 3-amino-2-fluoropyridine by diazotization of 3-amino-2-fluoropyridine with ethyl nitrite in fluoroboric acid. 3-amino-2-fluoropyridine in turn is prepared from 2-fluoropyridine-3-carboxamide by the Hofmann reaction. The yield of 2,3-difluoropyridine prepared by this process is very low (20%).

The dihalopyridine produced by the processes disclosed in the prior art is impure and requires several steps for extraction and isolation of the desired compound. In addition, the processes involve consumption of solvents in huge quantities, thereby making them costly and inappropriate for industrial production.

In light of the drawbacks of foregoing processes, and increasing demand for producing 2,3-dihalopyridines, there is a need to develop an alternate commercially and economically viable process for large scale manufacture of 2,3-dihalopyridine with high purity and yield. In addition the process should involve fewer purification steps and reduced quantity of solvents.

Therefore the present invention provides a solution to the aforesaid problems of the prior arts employing an improved process to produce dihalopyridine.

SUMMARY OF THE INVENTION

It is a principal object of the present invention to provide an improved process for producing 2,3-dihalopyridine, wherein the process enables production of highly pure 2,3-dihalopyridine at industrial scale with minimum generation of effluents.

It is another object of the present invention to provide a cost-effective and commercially viable process for producing 2,3-dihalopyridine, wherein the process employs minimum number of reaction steps and a minimum quantity of solvent during the extraction process.

It is a further object of the present invention to provide a process for producing 2,3-dihalopyridine, wherein the process comprises a minimum number of extraction steps to obtain pure 2,3-dihalopyridine.

It is yet another object of the present invention to provide a cost-effective and commercially viable process for producing 2,3-dihalopyridine, wherein the process enables reduction in time of operation of the process in plant.

The above and other objects of the present invention are further attained and supported by the following embodiments described herein. However, the scope of the invention is not restricted to the described embodiments herein after.

In accordance with one embodiment of the present invention, there is provided an improved industrial process for producing 2,3-dihalopyridine of formula (I), wherein the process comprises of halogenating 3-aminopyridine of formula (II) or salts thereof with halogenating agent in presence of ferric chloride, to obtain crude 3-amino-2-halopyridine of formula (III), diazotizing the 3-amino-2-halopyridine with a nitrite salt to obtain diazonium salt, reacting the diazonium salt with halo acid in presence of a copper (I) catalyst to form crude mass of 2,3-dihalopyridine of formula (I), separating undesired products from the crude mass by employing water immiscible organic solvent, and diluting the resultant mass employing water, followed by extraction employing water immiscible organic solvent to obtain 2,3-dihalopyridine of formula (I).

In accordance with another embodiment of the present invention, the 3-aminopyridine of formula (II) or salts thereof is produced by the process comprising of Hoffmann reaction of niacinamide.

In accordance with one other embodiment of the present invention, there is provided an improved industrial process for producing 2,3-dihalopyridine of formula (I), wherein the process comprises of halogenating 3-aminopyridine of formula (II) with halogenating agent in presence of ferric chloride, followed by filtration of the resultant mass at alkaline pH to obtain crude 3-amino-2-halopyridine of formula (III), dissolving the crude 3-amino-2-halopyridine employing a water immiscible organic solvent followed by filtration of the resultant and crystallizing the filtrate to obtain pure 3-amino-2-halopyridine of formula (III), diazotizing the 3-amino-2-halopyridine of formula (III) with a nitrite salt to obtain diazonium salt, reacting the diazonium salt with halo acid in presence of a copper (I) catalyst to form crude mass of 2,3-dihalopyridine of formula (I), separating undesired products from the crude mass by employing water immiscible organic solvent, and diluting the resultant mass employing water, followed by extraction employing water immiscible organic solvent to obtain 2,3-dihalopyridine of formula (I).

In accordance with another embodiment of the present invention, the alkaline pH is preferably between 9-11.

In accordance with still another embodiment of the invention there is provided a process for producing 2,3-dihalopyridine wherein the copper catalyst employed is having copper (I) oxidation state.

DETAILED DESCRIPTION OF THE INVENTION

While this specification concludes with claims particularly pointing out and distinctly claiming that, which is regarded as the invention, it is anticipated that the invention can be more readily understood through reading the following detailed description of the invention and study of the included examples.

The disclosed embodiments of the present invention deal with a process for producing 2,3-dihalopyridine of formula (I). The process of the present invention is advantageous over the prior art due to the utilization of industrially viable processing steps.

Additionally, the process is cost effective, involves minimum consumption of raw materials, solvents and minimum generation of effluents. The process further eliminates undesired processing steps, thereby making the process less time consuming, commercially viable and feasible for large-scale manufacture of pure 2,3-dihalopyridine (I). In addition, the process of the present invention involves reduction in batch cycle time thereby increasing the plant capacity, production and associated profits immensely.

According to a preferred embodiment of the present invention there is provided an improved process for industrial manufacturing of 2,3-dihalopyridine of formula (I) with high purity and yield.

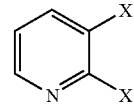
(I)

The process comprises of:
(a) halogenating 3-aminopyridine of formula (II) or salts thereof with halogenating agent in presence of ferric chloride to obtain crude 3-amino-2-halopyridine of formula (III);

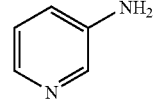
(II)

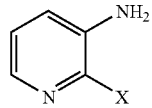
(III)

(b) diazotizing the 3-amino-2-halopyridine obtained in Step (a) with a nitrite salt to obtain diazonium salt;
(c) reacting the diazonium salt with halo acid in presence of a copper (I) catalyst to form crude mass of 2,3-dihalopyridine of formula (I);

(d) separating undesired products from the crude mass by employing water immiscible organic solvent; and (e) diluting the resultant mass employing water, followed by extraction employing water immiscible organic solvent to obtain 2,3-dihalopyridine of formula (I).

In accordance with another embodiment of the present invention, there is provided an improved process for industrial manufacturing of 2,3-dihalopyridine of formula (I) with high purity and yield, wherein 3-aminopyridine of formula (II) or salts thereof is produced by the process comprising of Hoffmann reaction of niacinamide.

The process according to the present invention, wherein the substitution X is any halogen selected from chlorine or bromine.

The copper (I) catalyst used herein the process of the present invention is selected from cuprous chloride, cuprous bromide or cuprous oxide.

The nitrite salt used herein the process is selected from sodium nitrite or potassium nitrite.

According to the process of the present invention, the extraction of crude 2,3-dihalopyridine from reaction mass is performed by separating the undesired products from the reaction mass by dissolving in a water immiscible organic solvent followed by diluting the separated mass with water, extracting the mass obtained at a higher temperature, preferably between 60-70° C. with a water immiscible organic solvent and isolating the product to obtain 2,3-dihalopyridine of formula (I) of high yield and purity.

The halogenating agent used herein the process of the present invention is selected from the group comprising hydrochloric acid and chlorine, hydrobromic acid and bromine, N-bromosuccinamide, sodium hypobromite or potassium hypobromite.

According to the process of the present invention, the water immiscible organic solvent is selected from the group comprising aromatic solvents, chloroform, carbon tetrachloride, ethyl acetate, butyl acetate and dichloromethane. The water immiscible organic solvent used herein is aromatic solvent. The aromatic solvent used herein is selected from the group comprising of benzene, toluene, xylenes, ethylbenzene. The water immiscible organic solvent employed during the process of the present invention is recyclable.

According to another preferred embodiment of the present invention there is provided an improved process for industrial manufacturing of 2,3-dihalopyridine of formula (I) with high purity and yield, the process comprising the steps of:

(a) halogenating 3-aminopyridine of formula (II) with halogenating agent in presence of ferric chloride, followed by filtration of the resultant mass at alkaline pH to obtain crude 3-amino-2-halopyridine of formula (III);

(b) dissolving the crude 3-amino-2-halopyridine of formula (III) employing a water immiscible organic solvent followed by filtration of the resultant;

(c) crystallizing the filtrate of step (b) to obtain pure 3-amino-2-halopyridine of formula (III);

(d) diazotizing the 3-amino-2-halopyridine with a nitrite salt to obtain diazonium salt;

(e) reacting the diazonium salt with halo acid in presence of a copper (I) catalyst to form crude mass of 2,3-dihalopyridine of formula (I);

(f) separating undesired products from the crude mass by employing water immiscible organic solvent; and (g) diluting the resultant mass employing water, followed by extraction employing water immiscible organic solvent to obtain 2,3-dihalopyridine of formula (I).

According to the process of the present invention, the pH of the reaction mass containing 3-amino-2-halopyridine is made alkaline, preferably adjusted between 9-11 and the mass separated by filtration. The resultant mass so obtained is dissolved in a water immiscible organic solvent, filtered to remove impurities and crystallized to obtain 3-amino-2-halopyridine of formula (II) of purity $\geqq 95\%$.

The process according to the present invention, wherein the substitution X is any halogen selected from chlorine or bromine.

The copper (I) catalyst used herein the process of the present invention is selected from cuprous chloride, cuprous bromide or cuprous oxide.

The nitrite salt used herein the process is selected from sodium nitrite or potassium nitrite.

The halogenating agent used herein the process of the present invention is selected from the group comprising hydrochloric acid and chlorine, hydrobromic acid and bromine, N-bromosuccinamide, sodium hypobromite or potassium hypobromite.

According to the process of the present invention, the extraction of crude 2,3-dihalopyridine from reaction mass is performed by separating the undesired products from the reaction mass by dissolving in a water immiscible organic solvent followed by diluting the separated mass with water, extracting the mass obtained at a higher temperature, preferably between 60-70° C. with a water immiscible organic solvent and isolating the product to obtain 2,3-dihalopyridine of formula (I) of high yield and purity.

According to the process of the present invention, the water immiscible organic solvent is selected from the group comprising aromatic solvents, chloroform, carbon tetrachloride, ethyl acetate, butyl acetate and dichloromethane. The water immiscible organic solvent used herein is aromatic solvent. The aromatic solvent used herein is selected from the group comprising of benzene, toluene, xylenes, ethylbenzene. The water immiscible organic solvent employed during the process of the present invention is recyclable.

In accordance with still another embodiment of the present invention, wherein the 2,3-dihalopyridine of formula (I) produced by the process of the present invention is characterized by having HPLC purity of more than 98% and GC purity of more than 99%.

The present invention is further illustrated below with reference to the following examples with out intending to limit the scope of the invention in any manner.

Example 1

One Pot Process for the Preparation of 2,3-dichloropyridine

Sodium hypochlorite (1120 g, 1.8 mol) was added to a mixture of nicotinamide (200 g, 1.64 mol) and DM water (700 g) in a RB flask under stirring at about 0° C. over 60 minutes. To this mixture aqueous sodium hydroxide (260 g, 3.0 mol) was added and the solution was heated and stirred at 90° C. for 2 hrs. Concentrated hydrochloric acid (468 g, 4.23 mol) was then added and the mixture was concentrated to obtain crude 3-aminopyridine solution. To this crude 3-aminopyridine solution, concentrated hydrochloric acid (1200 g, 10.85 mol) was added again at 0° C., followed with ferric chloride (5.5 g, 0.034 mol). The chlorine gas was then spurged (125 g, 1.78 mol) at room temperature. The resulting solution was cooled to about −8° C. and a solution of sodium nitrite (105 g, 1.52 mol) in water (140 ml) was added over 2-3 hrs. The resulting mixture was charged to a mixture containing cuprous chloride (109 g, 1.1 mol) and concentrated hydrochloric acid (440 g, 3.98 mol) at about 60-70° C. The completion of the reaction was monitored by HPLC. After the completion of reaction, the toluene was charged in reaction mass and undesired products were extracted in organic phase and discarded. The separated aqueous mass was diluted with DM water, extracted with toluene. Toluene is concentrated to dryness to obtain 136 g of white powder of 2,3-dichloropyridine (56% yield); Melting point 64° C. to 67° C.; HPLC purity 98.8%; GC purity 99.1% The toluene was kept aside for recycling. The product was confirmed by mass spectroscopy and $^1$H NMR.

ms:m/e 149(M+); $^1$H NMR (CDCl$_3$) δ 7.77 ppm (d, 4H, 1H), δ 7.20 ppm (dd, 5H, 1H), δ 8.31 ppm (d, 6H, 1H).

Example 2

Preparation of 3-amino-2-chloropyridine

3-Aminopyridine (25 g, 0.265 mols) was added to DM water (50 g) in a RB flask under stirring at 25-30° C. To this mixture concentrated aqueous hydrochloric acid (207 g, 1.7 mols) and ferric chloride (1.0 g, 0.006 mols) were added. Chlorine gas was then sparged into the reaction mass. The completion of the reaction was monitored by HPLC. After the completion of reaction, the pH of the crude mass was adjusted to 9-11 with sodium hydroxide solution and filtered. The crude mass was than dissolved in toluene at 65-75° C., filtered and concentrated to give 25.63 g of 3-amino-2-chloro-pyridine (75% yield) which contain about 2-3% of 3-amino-2,6-dichloropyridine by %area HPLC. Melting point: 76° C. to 78° C.; HPLC purity 96.4%. The toluene was kept aside for recycling. The product was confirmed by mass spectroscopy and $^1$H NMR.

ms:m/e 129(M+); $^1$H NMR (DMSO-D6) δ 7.12-7.07 ppm (m, 4H; 6H, 2H), δ 7.56 ppm (dd, 5H, 1H), δ 5.56 ppm (s, br, 3H, NH$_2$).

Example 3

Preparation of 2,3-dichloropyridine

To the flask was charged 3-amino-2-chloro-pyridine (25 g, 0.194 mol), obtained in Example 2, and aqueous hydrochloric acid (235 g, 1.9 mol). After the mixture was cooled to −8 to −3° C., a solution of sodium nitrite (16.15 g, 0.234 mol) in water (24 g) was added over 2-3 hours. This diazonium chloride salt mixture was transferred to an addition funnel and added to the flask containing aqueous hydrochloric acid (95 g, 0.78 mol) and cuprous chloride (27 g, 0.272 mol) at 60-70° C. The completion of the reaction was monitored by HPLC. After the completion of reaction, the toluene was charged in reaction mass and undesired products were extracted in organic phase and discarded. The separated aqueous mass was diluted with DM water, extracted with toluene. Toluene is concentrated to dryness to obtain 21.44 g of 2,3-dichloropyridine (75% yield); Melting point 64° C. to 67° C.; HPLC purity 98.6%. The toluene was kept aside for recycling. The product was confirmed by mass spectroscopy and $^1$H NMR.

ms:m/e149(M$^+$); $^1$H NMR (DMSO-D6) δ 8.17-8.15 ppm (dd, 4H, 1H), δ 8.42-8.40 ppm (dd, 6H, 1H), δ 7.51-7.48 ppm (m, 5H, 1H).

While this invention has been described in detail with reference to certain preferred embodiments, it should be appreciated that the present invention is not limited to those precise embodiments rather, in view of the present disclosure, which describes the current best mode for practicing the invention, many modifications and variations would present themselves to those skilled in the art without departing from the scope and spirit of this invention. This invention is susceptible to considerable variation in its practice within the spirit and scope of the appended claims.

We claim:

1. A process for preparing a 2,3-dihalopyridine of formula (I):

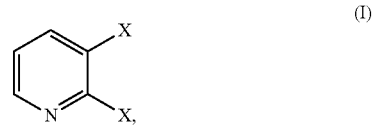

the process comprising:
(a) halogenating a 3-aminopyridine of formula (II) or a salt thereof with a halogenating agent in the presence of ferric chloride to obtain a crude 3-amino-2-halopyridine of formula (III):

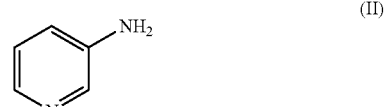

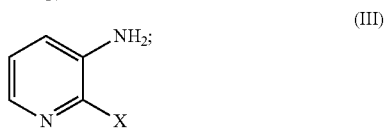

(b) diazotizing the crude 3-amino-2-halopyridine of formula (III) with a nitrite salt to obtain a diazonium salt;
(c) reacting the diazonium salt with a halo acid in presence of a copper (I) catalyst to form a crude mass of the 2,3-dihalopyridine of formula (I);
(d) separating undesired products from the crude mass by combining the crude mass with a water immiscible organic solvent and extracting an organic phase comprising the undesired products to yield a resultant aqueous mass; and
(e) diluting the resultant aqueous mass with water, followed by extraction with the same or another water immiscible organic solvent to obtain the 2,3-dihalopyridine of formula (I).

2. The process according to claim 1, further comprising forming the 3-aminopyridine of formula (II) by Hoffmann reaction of niacinamide, wherein the process is a one-pot process.

3. The process according to claim 1, wherein the X is chlorine or bromine.

4. The process according to claim 1, wherein the halogenating agent is selected from the group consisting of
hydrochloric acid and chlorine,
hydrobromic acid and bromine,
N-bromosuccinamide,
sodium hypobromite, and
potassium hypobromite.

5. The process according to claim 1, wherein the water immiscible organic solvent is selected from the group consisting of an aromatic solvent, chloroform, carbon tetrachloride, ethyl acetate, butyl acetate and dichloromethane.

6. The process according to claim 5, wherein the water immiscible organic solvent is an aromatic solvent.

7. The process according to claim 6, wherein the water immiscible organic solvent is selected from the group consisting of benzene, toluene, xylenes, and ethyl benzene.

8. The process according to claim 1, wherein the nitrite salt is selected from the group consisting of sodium nitrite and potassium nitrite.

9. The process according to claim 1, wherein the copper (I) catalyst is selected from the group consisting of cuprous chloride, cuprous bromide and cuprous oxide.

10. The process according to claim 1, wherein the halo acid is selected from the group consisting of hydrochloric acid and hydrobromic acid.

11. The process according to claim 6, wherein the extraction (d), the extraction (e), or both extractions (d) and (e), are carried out at a temperature range of 60 to 70° C.

12. A process for preparing a 2,3-dihalopyridine of formula (I):

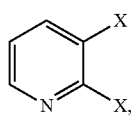
(I)

the process comprising:
(a) halogenating a 3-aminopyridine of formula (II) with a halogenating agent in presence of ferric chloride, followed by filtration of a resultant mass at an alkaline pH to obtain a crude 3-amino-2-halopyridine of formula (III),

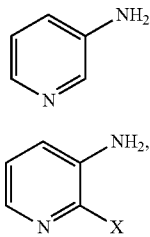

(b) dissolving the crude 3-amino-2-halopyridine of formula (III) with a water immiscible organic solvent followed by filtration of a resulting mixture to yield a filtrate;
(c) crystallizing the filtrate to obtain a purified 3-amino-2-halopyridine of formula
(d) diazotizing the purified 3-amino-2-halopyridine of formula (III) with a nitrite salt to obtain a diazonium salt;
(e) reacting the diazonium salt with a halo acid in the presence of a copper (I) catalyst to form a crude mass of the 2,3-dihalopyridine of formula (I);
(f) separating undesired products from the crude mass by combining the crude mass with the same or another water immiscible organic solvent and extracting an organic phase comprising the undesired products to yield a resultant aqueous mass; and
(g) diluting the resultant aqueous mass with water, followed by extraction with the same or another water immiscible organic solvent to obtain the 2,3-dihalopyridine of formula (I).

13. The process according to claim 12, wherein the alkaline pH is between 9-11.

14. The process according to claim 12, wherein the X is chlorine or bromine.

15. The process according to claim 12, wherein the halogenating agent is selected from the group consisting of
hydrochloric acid and chlorine,
hydrobromic acid and bromine,
N-bromosuccinamide,
sodium hypobromite, and
potassium hypobromite.

16. The process according to claim 12, wherein the water immiscible organic solvent is selected from the group consisting of an aromatic solvent, chloroform, carbon tetrachloride, ethyl acetate, butyl acetate and dichloromethane.

17. The process according to claim 16, wherein the water immiscible organic solvent is an aromatic solvent.

18. The process according to claim 17, wherein the aromatic solvent is selected from the group consisting of benzene, toluene, xylenes, and ethylbenzene.

19. The process according to claim 12, wherein the nitrite salt is sodium nitrite or potassium nitrite.

20. The process according to claim 12, wherein the copper (I) catalyst is selected from the group consisting of cuprous chloride, cuprous bromide and cuprous oxide.

21. The process according to claim 12, wherein the halo acid is hydrochloric acid or hydrobromic acid.

22. The process according to claim 17, wherein the extraction (f), the extraction (g), or both extractions (f) and (g), are carried out at a temperature range of 60 to 70° C.

23. The process according to claim 2, wherein:
the water immiscible organic solvent is an aromatic solvent;
the extraction (d), the extraction (e), or both extractions (d) and (e), are carried out at a temperature range of 60 to 70° C.; and
the 2,3-dihalopyridine is obtained with HPLC purity of greater than 98.5%, based on an amount of the niacinamide reacted.

* * * * *